United States Patent
Nielsen et al.

(10) Patent No.: US 10,946,144 B2
(45) Date of Patent: Mar. 16, 2021

(54) POWER EFFICIENT ACCESSORY DEVICE

(71) Applicant: Novo Nordisk A/S, Bagsvaerd (DK)

(72) Inventors: Dan Groenkjaer Nielsen, Copenhagen (DK); Nikolai Byskov, Noerrebro (DK)

(73) Assignee: Novo Nordisk A/S, Bagsvaerd (DK)

( * ) Notice: Subject to any disclaimer, the term of this patent is extended or adjusted under 35 U.S.C. 154(b) by 16 days.

(21) Appl. No.: 16/081,365

(22) PCT Filed: Feb. 27, 2017

(86) PCT No.: PCT/EP2017/054493
§ 371 (c)(1),
(2) Date: Aug. 30, 2018

(87) PCT Pub. No.: WO2017/148857
PCT Pub. Date: Sep. 8, 2017

(65) Prior Publication Data
US 2019/0083714 A1  Mar. 21, 2019

(30) Foreign Application Priority Data

Mar. 1, 2016 (EP) .................................. 16157985

(51) Int. Cl.
| | | |
|---|---|---|
| *A61M 5/31* | (2006.01) | |
| *A61M 5/315* | (2006.01) | |
| *A61M 5/20* | (2006.01) | |
| *G06K 9/18* | (2006.01) | |
| *G16H 40/63* | (2018.01) | |
| *G16H 20/17* | (2018.01) | |
| *A61M 5/24* | (2006.01) | |

(52) U.S. Cl.
CPC .......... *A61M 5/31553* (2013.01); *A61M 5/20* (2013.01); *A61M 5/31568* (2013.01);
(Continued)

(58) Field of Classification Search
CPC ................ A61M 5/31553; A61M 5/20; A61M 5/31568; A61M 5/31583;
(Continued)

(56) References Cited

U.S. PATENT DOCUMENTS

| | | |
|---|---|---|
| 6,585,698 B1 | 7/2003 | Packman et al. |
| 10,471,213 B2 | 11/2019 | Schabbach et al. |

(Continued)

FOREIGN PATENT DOCUMENTS

| | | |
|---|---|---|
| CN | 104436371 A | 3/2015 |
| JP | 2001170176 A | 6/2001 |

(Continued)

*Primary Examiner* — Amber R Stiles
(74) *Attorney, Agent, or Firm* — Wesley Nicolas (57) ABSTRACT

An add-on device adapted to be releasably attached to a drug delivery device, the drug delivery device comprising an indicator adapted to display a dose amount during dose setting, and to display the remaining dose amount to be expelled during drug expelling. The add-on device comprises an electronically controlled display adapted to display a set dose amount, a sensor assembly adapted to detect movement of the dose setting member when the add-on device is attached to a drug delivery device, a camera device adapted to capture an image of the indicator, and processor means adapted to (i) control the display dynamically to show the set dose amount based on input from the sensor assembly, and (ii) determine an expelled dose amount based on input from the camera device.

15 Claims, 6 Drawing Sheets

(52) U.S. Cl.
CPC .......... *A61M 5/31583* (2013.01); *G06K 9/18* (2013.01); *G16H 20/17* (2018.01); *G16H 40/63* (2018.01); *A61M 2005/2407* (2013.01); *A61M 2205/8212* (2013.01)

(58) Field of Classification Search
CPC .. A61M 2005/2407; A61M 2205/8212; G16H 40/63; G16H 20/17; G06K 9/18
See application file for complete search history.

(56) References Cited

U.S. PATENT DOCUMENTS

| | | |
|---|---|---|
| 2009/0318865 A1 | 12/2009 | Moller et al. |
| 2012/0072236 A1 | 3/2012 | Atkin |
| 2019/0192780 A1 | 6/2019 | Cowe |

FOREIGN PATENT DOCUMENTS

| | | | | |
|---|---|---|---|---|
| JP | 2012519026 A | 8/2012 | | |
| JP | 2015528318 A | 9/2015 | | |
| WO | 2010/052275 A2 | 5/2010 | | |
| WO | 2011/117212 A1 | 9/2011 | | |
| WO | 2013004844 A1 | 1/2013 | | |
| WO | 2013120776 A1 | 8/2013 | | |
| WO | 2014/020008 A1 | 2/2014 | | |
| WO | 2014037331 A1 | 3/2014 | | |
| WO | WO-2014037331 A1 * | 3/2014 | .............. | A61M 5/24 |
| WO | 2014/111340 A1 | 7/2014 | | |
| WO | 2014/161952 A1 | 10/2014 | | |
| WO | 2014173768 A1 | 10/2014 | | |

* cited by examiner

POWER EFFICIENT ACCESSORY DEVICE

CROSS-REFERENCE TO RELATED APPLICATIONS

This application is a 35 U.S.C. § 371 National Stage application of International Application PCT/EP2017/054493 (published as WO 2017/148857), filed Feb. 27, 2017, which claims priority to European Patent Application 16157985.9, filed Mar. 1, 2016, the contents thereof which are incorporated by reference in their entirety.

The present invention generally relates to medical devices for which the generation, collecting and storing of data are relevant. In specific embodiments the invention relates to devices and systems for capturing and organizing drug delivery dose data in a reliable, user-friendly and power efficient way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices being either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2014/037331 describes in a first embodiment an electronic supplementary device (also named "add-on module" or "add-on device") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialed into the drug delivery device. WO 2014/037331 also describes a second embodiment of an electronic supplementary device adapted to be releasably attached to a drug delivery device of the pen type comprising a drive screw extending proximally from the device corresponding to a set dose. The supplementary device comprises sensor means for determining axial extension of the drive screw as well as sensor means for detecting operation of the proximal delivery button. WO 2014/020008 discloses an electronic supplementary device adapted to be releasably attached to a drug delivery device of the pen type. The device includes a camera and is configured to determine scale drum values based on OCR. To properly determine the size of an expelled dose the supplementary device further comprises additional electromechanical sensor means to determine whether a dose size is set, corrected or delivered. A further external device for a pen device is shown in WO 2014/161952. As the external device is designed to detect signals or events originating from the device to which it is attached it is important that the two devices are correctly positioned relatively to each other to ensure proper operation and prevent incorrect measurements.

Having regard to the above, it is an object of the present invention to provide devices and methods allowing secure, easy and power efficient operation of a drug delivery assembly comprising a user-mountable module.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention an add-on device adapted to be releasably attached to a drug delivery device is provided, the drug delivery device comprising a housing, a drug reservoir or means for receiving a drug reservoir, drug expelling means comprising a moveable dose setting member allowing a user to set a dose amount of drug to be expelled, actuation member actuatable between a first and a second state, the first state allowing a dose amount to be set, the second state allowing the drug expelling means to expel a set dose, and an indicator adapted to display the set dose amount during dose setting, and to display the remaining dose amount to be expelled during drug expelling. The add-on device comprises mounting means, an electronically controlled display adapted to display a set dose amount, a sensor assembly adapted to detect movement of the dose setting member when the add-on device is attached to a drug delivery device, a camera device adapted to capture an image of the indicator, and processor means adapted to (i) control the display dynamically to show the set dose amount based on input from the sensor assembly, and (ii) determine an expelled dose amount based on input from the camera device.

By the above arrangement an add-on device adapted to be releasably attached to a drug delivery device in order to determine an expelled dose amount is provided, the add-on device being both reliable and power efficient during operation.

In an exemplary embodiment an expelled dose amount is determined based on a first feature captured from a first image and a second feature captured from a second image, the first image being captured when a dose amount has been set and the second image being captured when a dose amount has been expelled. The first feature may be used to determine a first position of the indicator, and the second feature may be used to determine a second position of the indicator, the positional difference between the first and second positions being indicative of an expelled amount of drug.

The processor may be adapted to control the camera to capture a first image when no input has been received from the sensor assembly for a predetermined amount of time after the last input.

The add-on device may further comprise switch means adapted to detect when the actuation member is actuated from the second to the first state, wherein the processor is adapted to control the camera to capture a second image when the switch means detects that the actuation member is actuated from the second to the first state.

In an exemplary embodiment the add-on device comprises a main portion adapted to be releasably attached to the housing, and a dial portion adapted to be releasably attached, directly or indirectly, to the moveable dose setting member. The sensor assembly comprises a first portion coupled to the main portion, and a second portion coupled to the dial portion, wherein the sensor assembly is adapted to detect rotational movement between the first and second portion.

In an exemplary embodiment the add-on device is adapted to cover the dose setting member when attached to a drug delivery device, and the dial portion is adapted to be gripped by the user to thereby move the dose setting member. The dial portion may be adapted to rotate to thereby rotate the dose setting member, and the sensor assembly may be a rotary sensor assembly. Alternatively the sensor assembly may be an axial sensor assembly adapted to detect axial movement of a drive screw being moved proximally out of the drug delivery device during dose setting.

In an exemplary embodiment the dial portion has an initial axial position, i.e. when mounted on the drug delivery device with no dose being set, and is restricted from being moved proximally relative to the main portion, such an arrangement being suitable for use together with a drug delivery device of the spring-driven type in which the dose setting member does only rotate during dose setting. Alternatively, the dial portion may be adapted to move proximally during dose setting, such an arrangement being suitable for use in combination with a drive screw being moved proximally out of the drug delivery device during dose setting.

The add-on device may further comprise a release portion adapted to be moved by the user between an initial and an actuated position, wherein the release portion with the add-on device attached to a drug delivery device is adapted to engage and move the actuation member. The add-on device may be adapted to cover the actuation member when attached to a drug delivery device.

In an exemplary embodiment the release portion is adapted to move axially relative to the rotatable dial portion, this allowing the dial portion to be coupled to and move axially together with the release portion.

The mounting means may comprise a bore adapted to receive a drug delivery device cylindrical portion, the bore comprising a mounting surface adapted to face the drug delivery device when in a mounted position, the mounting means further comprising locking means adapted to be moved into the bore to thereby engage a surface structure on the drug delivery device on which the add-on device is mounted.

Addressing the issue of secure and power efficient operation of an add-on device, the present invention provides in a second general aspect an add-on logging device configured to be releasably attached to a drug delivery device. Such a drug delivery device comprises a housing, a drug reservoir or means for receiving a drug reservoir, drug expelling means comprising a rotatable dose setting member allowing a user to set a dose amount of drug to be expelled, actuation member actuatable between a first and a second state, the first state allowing a dose amount to be set, the second state allowing the drug expelling means to expel a set dose, and a rotatable indicator adapted to display the set dose amount during dose setting, and to display the remaining dose amount to be expelled during drug expelling. The logging device comprises a sensor assembly adapted to detect rotational movement of the dose setting member when the logging device is attached to a drug delivery device, a camera device adapted to capture an image of the indicator, a memory adapted to store a reference position value corresponding to a rotational position of the indicator, and processor means adapted to (i) determine a current rotational position of the indicator based on: a captured image of the indicator, the stored reference position value, and the amount of rotational movement detected by the sensor assembly since the position value was stored, (ii) store the determined current rotational position in the memory as a new reference position value, and (iii) determine an expelled dose amount based on input from the camera. By this arrangement the position of the indicator can be determined faster and more power efficient.

In an exemplary embodiment the expelled dose amount is determined based on a first feature captured from a first image and a second feature captured from a second image, the first image being captured when a dose amount has been set and the second image being captured when a dose amount has been expelled. The first feature may be used to determine a first position of the indicator, and the second feature may be used to determine a second position of the indicator, the positional difference between the first and second positions being indicative of an expelled amount of drug.

Addressing the issue of secure and easy handling of an add-on device, the present invention provides in a further general aspect an add-on logging device configured to be releasably attached to a drug delivery device. Such a drug delivery device comprises a drug reservoir or means for receiving a drug reservoir, drug expelling means comprising a dose setting member allowing a user to set a dose amount of drug to be expelled, an actuation member actuatable between a first and a second state, the first state allowing a dose amount to be set, the second state allowing the drug expelling means to expel a set dose, an indicator member adapted to display the set dose amount during dose setting, and to display the remaining dose amount to be expelled during drug expelling, and a generally cylindrical housing portion comprising an opening allowing a user to observe a portion of the indicator member during dose setting, the opening being surrounded by an edge formed by the housing. The logging device comprises a bore adapted to receive the drug delivery device cylindrical portion, the bore comprising a mounting surface adapted to face the drug delivery device when in a mounted position, a camera opening formed in the mounting surface, a positioning structure protruding from the mounting surface and surrounding at least in part the camera opening, a camera adapted to capture an image of at least a portion of an indicator member arranged in alignment with the camera window, and a processor adapted to determine an expelled dose amount based on input from the camera, which may be in form of any image capturing device or assembly. By this arrangement the tolerance chain between the two essential components for determination of the size of an expelled dose, the camera and the indicator member, can be optimized.

In the present context the term bore is used to cover a structure into which the cylindrical portion of the drug delivery device can be inserted axially, i.e. the bore does not have to be able to fully enclose a given drug delivery device circumferentially just as the bore structure may span only a portion of the length of the add-on device.

In a more specific aspect of the invention an assembly comprising a logging device and a drug delivery device is provided, the logging device being adapted to be releasably mounted on the drug delivery device. The drug delivery device comprises a drug reservoir or means for receiving a drug reservoir, drug expelling means comprising a dose setting member allowing a user to set a dose amount of drug to be expelled, an actuation member actuatable between a first and a second state, the first state allowing a dose amount to be set, the second state allowing the drug expelling means to expel a set dose, an indicator member adapted to display the set dose amount during dose setting, and to display the remaining dose amount to be expelled during drug expelling, and a housing comprising an opening allowing a user to observe a portion of the indicator member, the opening being surrounded by an edge formed by the housing. The logging device comprises a housing having a mounting surface adapted to face the drug delivery device when in a mounted position, mounting means allowing the logging device to be mounted on the drug delivery device, a camera device adapted to capture an image of the indicator member as shown in the opening, a processor adapted to determine an expelled dose amount based on input from the camera device, wherein the logging device comprises a positioning structure protruding from the mounting surface and being adapted to engage at least portions of the opening edge to thereby position the logging device axially and rotationally relative to the opening.

The mounting surface may be provided with a camera opening surrounded at least in part by the positioning structure protruding from the mounting surface, the camera device being arranged to capture an image of the indicator member through the camera opening when the logging device is mounted on the drug delivery device. The drug delivery device may comprise a generally cylindrical housing portion in which the opening is formed, the logging device comprising a bore adapted to receive the drug delivery device cylindrical portion, the mounting surface forming at least a part of the bore.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsvrd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. The window is in the form of an opening in the housing surrounded by a chamfered edge portion 109 and a dose pointer 109P, the window allowing a portion of a helically rotatable indicator member 170 (scale drum) to be observed. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1A:
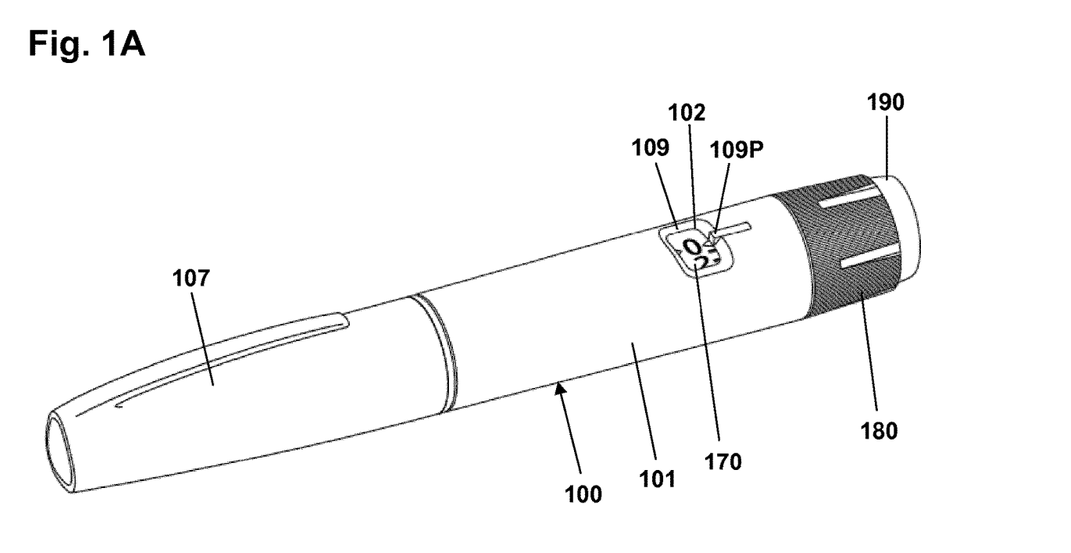
FIG. 1A shows a pen device.
Figure 1B:
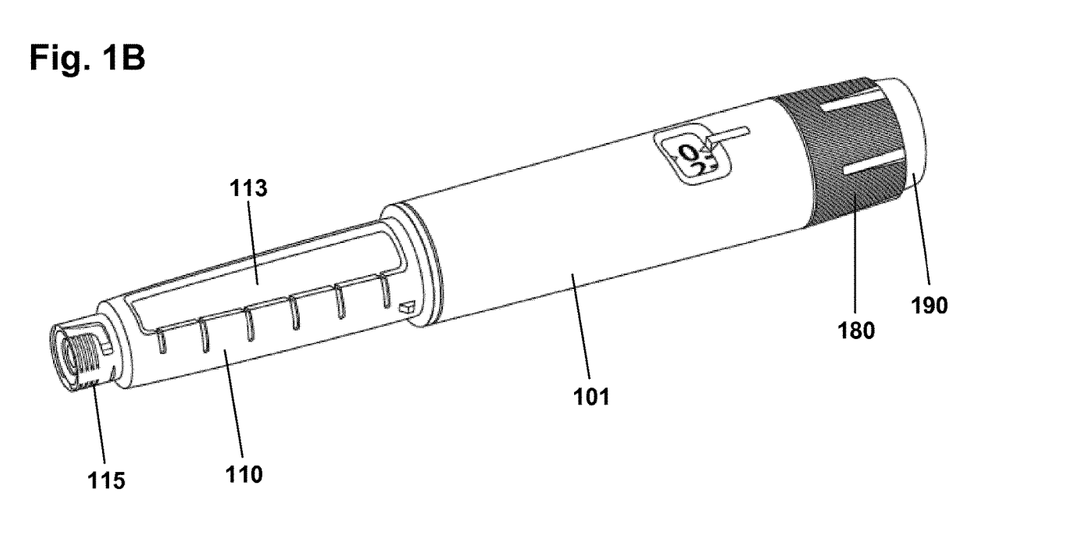
FIG. 1B shows the pen device of FIG. 1A with the pen cap removed.

Although FIG. 1 shows a drug delivery device of the prefilled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to interact with a drug delivery device, an exemplary embodiment of such a device will be described for better understanding of the invention.

Figure 2:
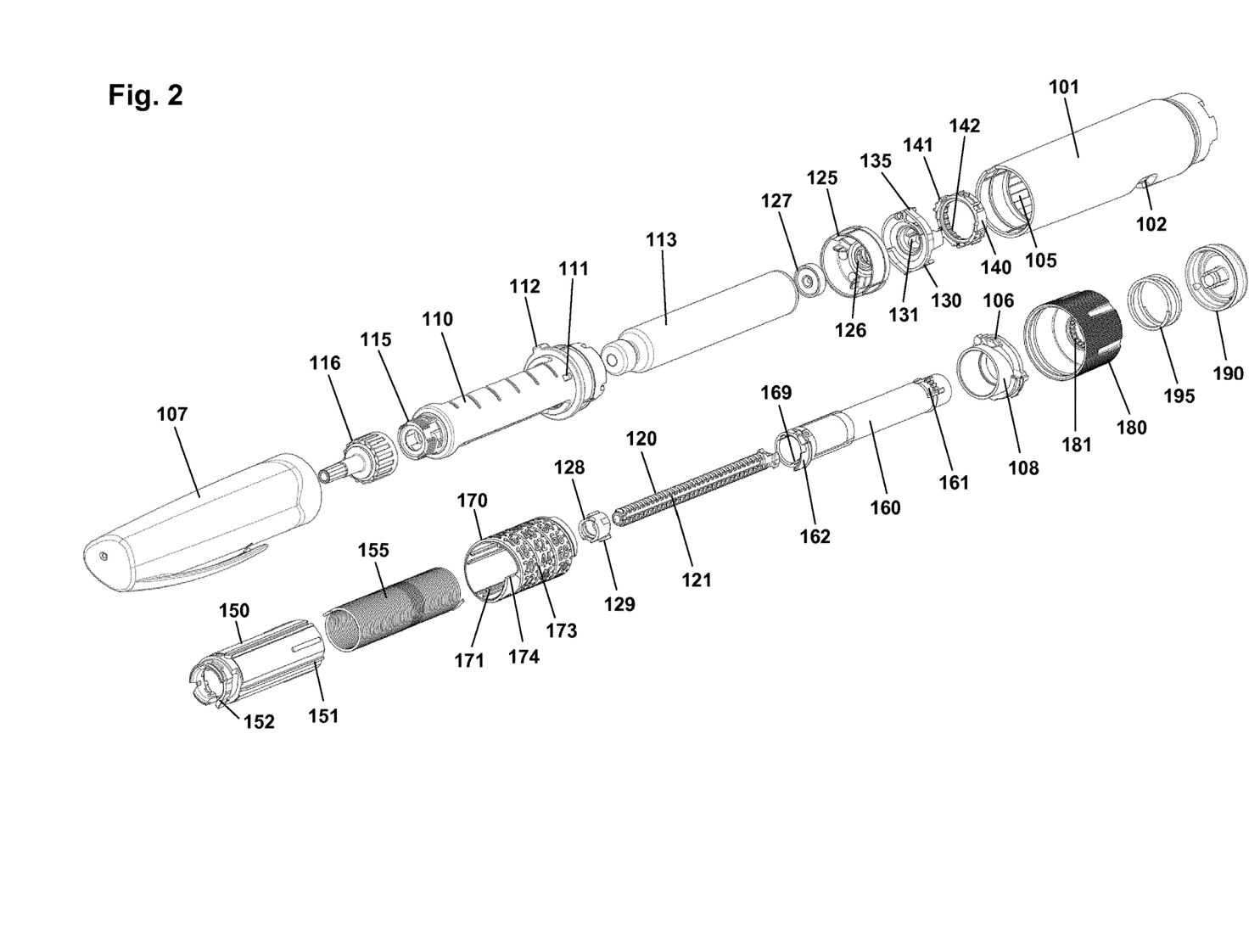
FIG. 2 shows in an exploded view the components of the pen device of FIG. 1A,
FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasably mounted, proximal coupling means in the form of two opposed protrusions 111 allowing a cap 107 to be releasably mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

Figure 3A:
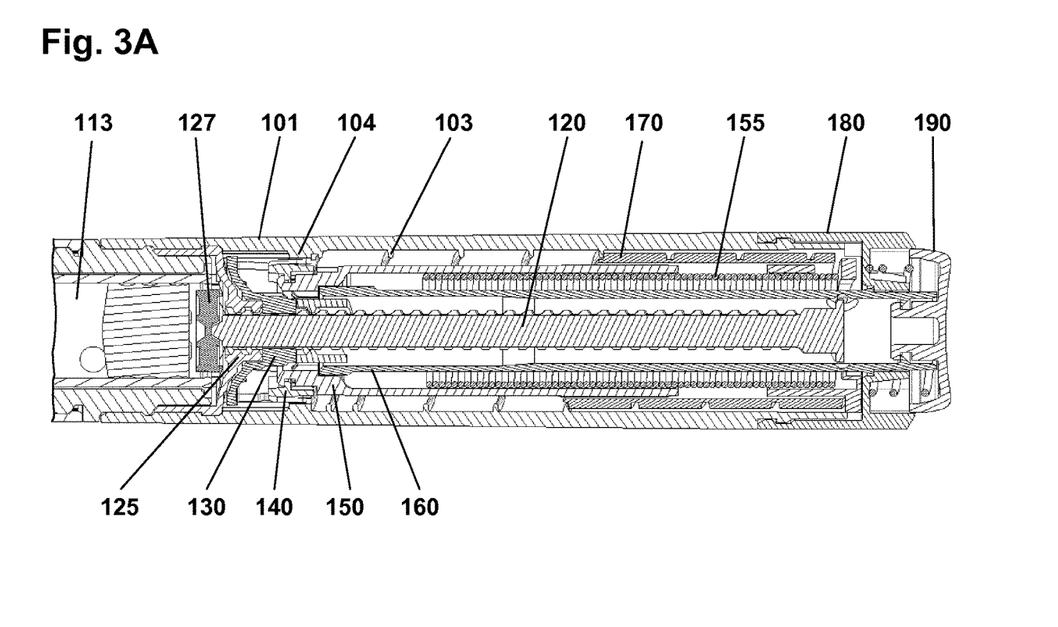

The dial system comprises a ratchet tube 150, a reset tube 160, a scale drum 170 with an outer helically arranged pattern forming a row of dose indicia, a user-operated dial member 180 for setting a dose of drug to be expelled, a release button 190 and a torque spring 155 (see FIG. 3). The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it. As the ratchet tube is connected to the distal end of the torque spring 155, the spring is loaded. During dose setting, the arm 152 of the ratchet performs a dial click for each unit dialed due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
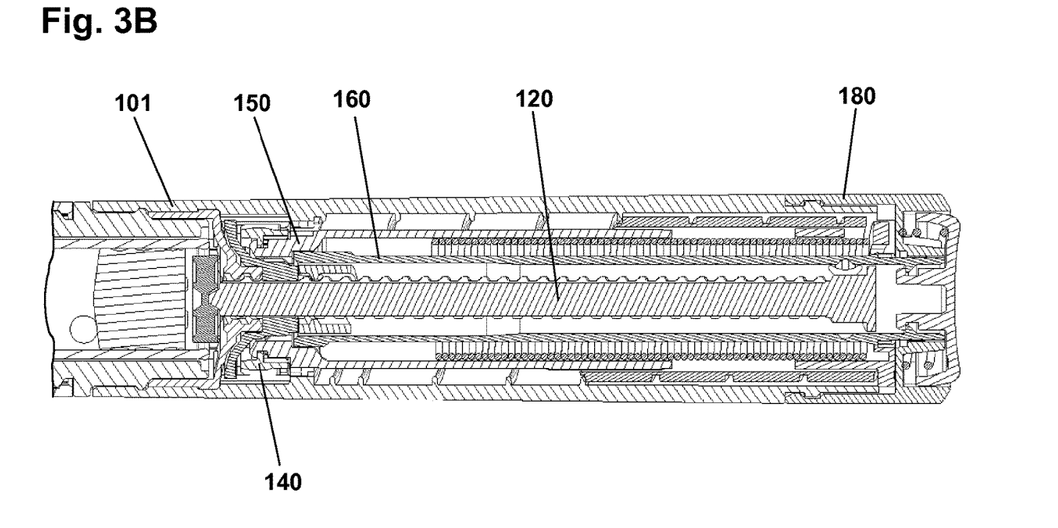

To deliver a set dose, the push button 190 is pushed in the distal direction by the user as shown in FIG. 3B. The reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 181 engaging a number of corresponding teeth arranged on a flexible carrier portion 161 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of the present invention will be described.

Figure 4:
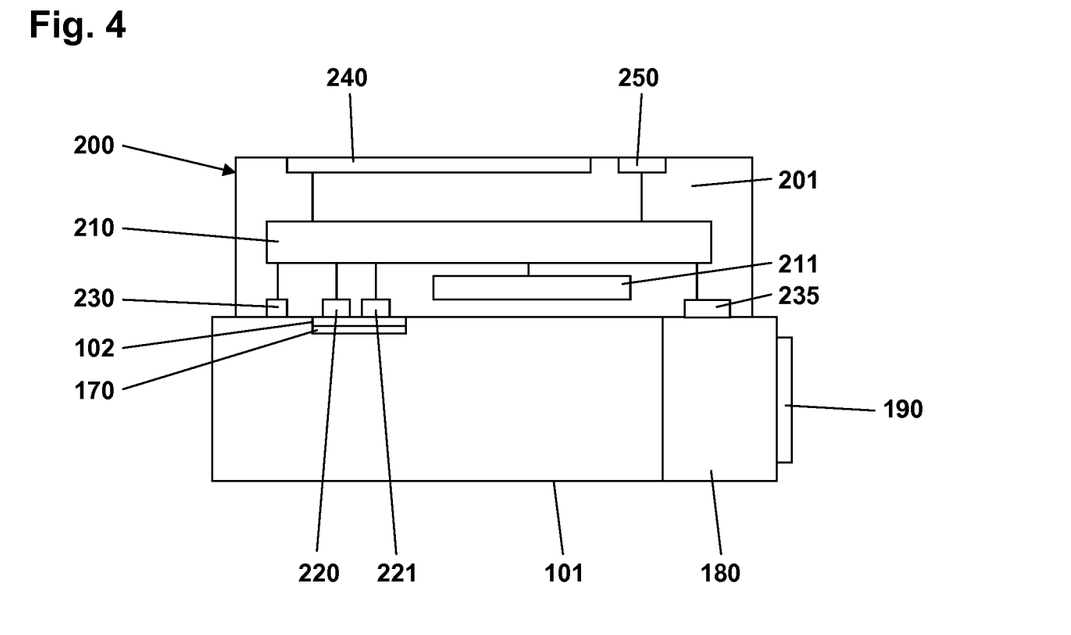
FIG. 4 shows a schematic representation of an add-on device.

FIG. 4 shows a schematic representation of an add-on device 200 in a state where it has been mounted on the housing 101 of a drug delivery device 100 of the above-described pen type. The add-on device is adapted to determine the amount of drug expelled from the drug delivery device during an expelling event, i.e. the subcutaneous injection of a dose of drug. In the shown embodiment determination of an expelled dose of drug is based on determination of scale drum position at the beginning and at the end of the expelling event. To determine the rotational position of the scale drum the dose numerals as seen in the display window 102 may be captured and used, this allowing an unmodified pen device to be used. Actual determination of scale drum position may be performed using e.g. optical character recognition (OCR) or template matching. The latter concept is described in greater detail in EP 15202796.7 which is hereby incorporated by reference. Alternatively a dedicated code pattern may be provided on the scale drum as disclosed in e.g. WO 2013/004843.

The add-on device comprises a housing 201 in which are arranged electronic circuitry 210 powered by an energy source 211. The electronic circuitry is connected to and interacts with a light source 220 adapted to illuminate at least a portion of the scale drum 170 seen in the window 102, a capture device (camera device) 221 adapted to capture image data from the scale drum, a low-power motion/position sensor assembly 235 designed to interface with the dose setting member 180 (see below), a mounting switch 230 adapted to engage the pen housing 101, a display 240 and user input means in the form of one or more buttons 250. Additionally an acoustic sensor may be provided to detect specific sounds generated by the expelling mechanism during dose setting and dose expelling. The electronic circuitry 210 will typically comprise controller means, e.g. in the form of a generic microprocessor or an ASIC, non-volatile program memory such as a ROM providing storage for embedded program code, writable memory such as flash memory and/or RAM for data, and a display controller. The electronic circuitry may also comprise one or more means of removing or communicating information stored in ROM or flash memory such as a wireless transmitter/receiver, a card slot or an output port, e.g. a USB port.

The add-on device further comprises mounting means (not shown) adapted to releasably mount and securely hold and position the add-on device on the pen housing. For the shown embodiment the add-on device covers the display window for which reason the current dose size shown in the display window has to be captured and displayed on the electronic display 240. Alternatively, the add-on device may be designed to allow the user to view the display window.

The coupling means may be in the form of e.g. a bore allowing the add-on device to slide in place on the pen body, flexible gripping structures allowing the add-on device to be mounted in a perpendicular direction, or locking means which has to be operated by the user, e.g. a hinged latch member or a sliding member. In order to securely hold and position the add-on device on the pen housing the add-on device may be provided with positioning means adapted to engage a corresponding positioning structure on the pen body. The positioning structure may be in the form of an existing structure provided for a different purpose, e.g. the window opening, or a specific mounting structure, e.g. one or more indents provided on the pen body.

As scale drum position and thus dose size determination is based on image capturing and subsequent processing of the captured image data, it is important that the add-on device is correctly positioned in its intended operational position on the drug delivery device. In addition to the above-described coupling and positioning means designed to provide a user-recognisable engagement, e.g. by an ensuring "click", the add-on device 200 is provided with a mounting switch 230, e.g. a mechanical micro switch, which is actuated from an off-state to an on-state when the add-on device is mounted on the pen housing.

As mentioned above, the add-on device is provided with a low-power motion/position sensor assembly 235 which is designed to control the display 240 during dose setting. In this way the relatively power-hungry camera device and light source do not have to be operated during dose setting to control the display but can be reserved to capture information relating to the expelled dose, this providing a longer battery life.

Depending on the desired level of device complexity, the user interface may be more or less user friendly, i.e. a high degree of user friendliness will normally require a high level of device complexity and a lower degree of user friendliness will normally require a lower level of device complexity.

A simple motion detector may be designed to interface mechanically or optically with the surface of the dose setting member 180 to detect incremental rotation corresponding to the size of a set dose. Although a dose setting member typically is provided with a plurality of longitudinal ridges or grooves to provide a good grip for the user, these structures will in most cases not have been designed to correspond to the rotational dose increments for the given pen, e.g. a rotation of 15 degrees for each increment of 1 unit of insulin (IU). To overcome this situation the add-on module may be provided with a rotational sensor ring member having an inner surface adapted to non-rotationally engage the dose setting member and an outer (interior) surface having an "incremental pattern" adapted to interface with corresponding low-power motion/position sensor means arranged in the add-on module. The sensor means may be a mechanical switch actuated by grooves/ridges on the sensor ring member or an optical sensor adapted to sense an incremental pattern on the sensor ring member, e.g. more or less reflective areas. Alternatively, instead of a sensor ring member, a rotational wheel member may engage the dose setting member or the sensor ring member (like in a traditional ball-based computer mouse). The latter arrangement has the advantage that it would be relatively simple to detect when a set dose is adjusted by dialing down. If the sensor system is based on an incremental mechanical switch such a switch would have to be designed to detect rotational direction to cope with a dial down situation.

In the above-described incremental counter set-up two conditions have to be met in order to correctly detect the size of a dialed dose and control the display correspondingly, i.e. the sensor system has to be operational from the initial rotational movement and the sensor system has to know the starting point, i.e. typically, but not necessarily, the initial zero position. Although a mechanical switch could be used to wake up the system, this may not be sufficiently fast to detect initial movement.

To overcome these issues the add-on device may be designed to require a specific initial user-input in order to work properly. For example, the user may be instructed to initially dial a given dose of e.g. at least 10 IU and then dial back the dose setting member 180 to the zero stop position, which would allow the sensor system to power up and perform a camera based position check to ensure that the scale drum is showing "0". When this is confirmed an "OK" or similar message may be displayed on add-on module display. The user can now dial a dose by rotating the dose setting member whereby the incremental sensor system will detect each increment and control the display correspondingly.

When it is detected that dial movement has stopped, e.g. no motion input in two seconds, the camera device will capture an image of the scale drum which can then be processed to determine the "true" actual rotational position of the scale drum which may then be displayed. This may be indicated in the display by a symbol. As appears, depending on how accurate dial motion was detected during the dose setting the hitherto displayed dose size value may be adjusted. If then desired the user may re-adjust the set dose size resulting in a new image capture. As the shown system of FIG. 4 is not provided with sensor means for detecting actuation of the release button 190 the system will have detect an end-of-dose state alternatively. For example, the system may comprise an acoustic sensor adapted to detect a specific sound associated with an end-of-dose state, e.g. a distinctive end-of-dose click as produced by the Flex-Touch® pen from Novo Nordisk. When this sound is identified the camera device may capture an image which may then be processed to determine whether the scale drum has returned to the zero position. If this is the case the expelled dose will be displayed on the display and stored in the memory in combination with a time stamp to provide a log entry. If no end-of-dose indicator is detected the system may time-out after e.g. 5 minutes and a corresponding message displayed in the display.

In the alternative the add-on device may be designed to provide a higher degree of user friendliness and be less focused on low system complexity.

Figure 5:
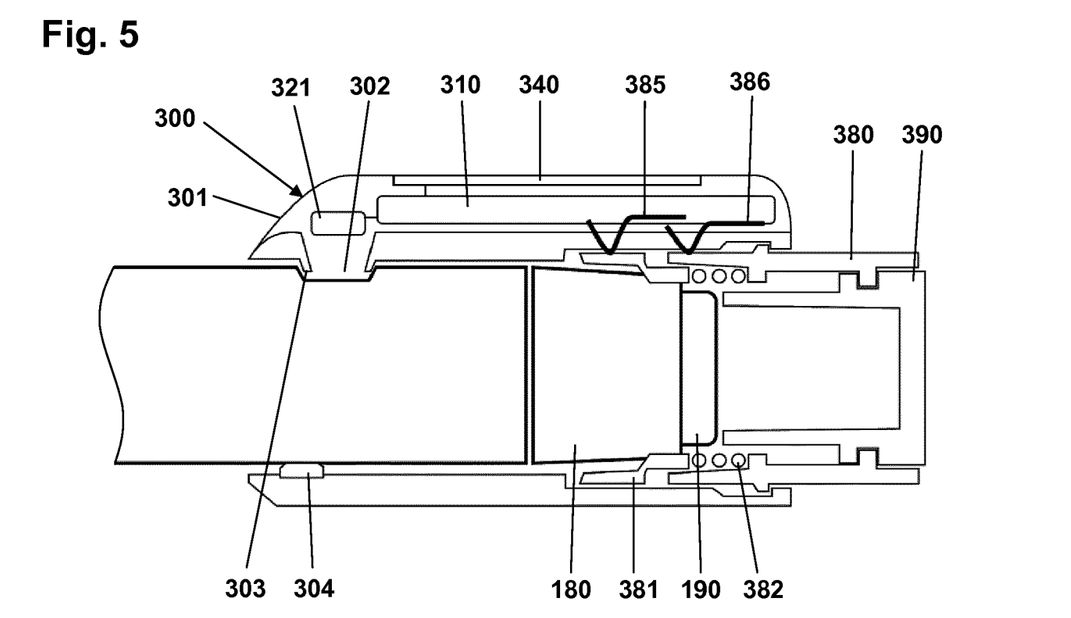
FIG. 5 shows an add-on device mounted on the housing of a drug delivery device.

Turning to FIG. 5 a second embodiment of an add-on module 300 is shown, the module comprising a position sensor assembly in combination with a state switch actuated by a release member provided as part of the module. More specifically, the add-on module 300 comprises a housing 301 in which are arranged electronic circuitry 310, an energy source, a light source, a camera device 321 and a display 340, this generally corresponding to the components of the add-on module shown in FIG. 4. The add-on module housing forms a bore adapted to receive the generally cylindrical proximal portion of the pen device, the bore being defined by a generally cylindrical mounting surface adapted to face the pen device. A camera opening 302 is formed in the mounting surface. A small clearance is provided between the bore and the pen to allow the pen to be received in the bore. A firm grip between the two structures is provided by a locking structure 304 on the add-on module adapted to engage the pen device and securing a firm grip. The locking structure may be spring biased and adapted to snap in place when the add-on module is mounted on the pen. Alternatively the locking structure may be in the form of a user-operated lock. The add-on module comprises a positioning structure 303 protruding from the mounting surface and being adapted to engage at least portions of the opening edge to thereby position the add-on module both axially and rotationally relative to the opening. In the shown embodiment the positioning structure is in the form of a protruding lip 303 structure surrounding at least partially the camera opening, the lip structure being adapted to form-fitting engage the edge portion of the window opening to thereby ensure correct positioning both axially and rotationally between the two housing structures and thereby between the camera device and the scale drum.

Additionally, the add-on module 300 is provided with a user accessible add-on dial member 380, a user accessible add-on release button 390, a position sensor assembly comprising a cylindrical code member 381 in combination with a code contact array 385, and a state switch 386 associated with the add-on dial member. In the shown embodiment the mounting switch functionality is integrated in the position sensor assembly, see below. In the shown embodiment the add-on dial member 380 and the add-on release button 390 is mounted axially locked to each other to form a combined add-on dial and release member. Alternatively the add-on dial member 380 may be axially locked relative to the housing 301 with the add-on release button 390 being arranged to move axially relative to the add-on dial member. The two members may also be rotationally locked to each other. As appears, when the add-on module is mounted on the pen device the pen dose setting member and the pen release button are covered by the add-on module.

The cylindrical code member 381 has an inner surface adapted to axially engage the dose setting member 180 when the add-on device is mounted on the pen device, the mating surfaces providing non-rotational engagement, e.g. based on the axially oriented groove pattern provided on the Flex-Touch® pen device as shown in FIG. 1A. The add-on dial member 380 is coupled freely rotatable to the module housing 301 but is in non-rotational engagement with the code member 381 and thus the dose setting member 180 when the add-on module is mounted on the pen device. The add-on dial member 380 is arranged to be moved axially relative to the module housing between an initial proximal-most position and an actuated distal-most position. A bias spring 382 is provided between the code member 381 and the add-on dial member 380 to ensure that the combined add-on member is biased towards its proximal-most position. The add-on release button portion 390 of the combined add-on member is adapted to engage the pen device release button 190 when moved axially relative to the module housing. In this way a dose is set by means of the add-on dial member portion 380 and a set dose is released by means of the add-on release button portion 390.

The position sensor assembly comprises the above-described generally cylindrical code member having an outer circumferential surface provided with a Gray code pattern rotating together with the add-on dial member 380, and a contact assembly comprising a number of galvanic contact members in sliding engagement with the code pattern surface. The output from the position sensor assembly is decoded by the processor and a rotational position is determined which is then used to control the display. The position sensor may be "absolute" having a resolution corresponding to the number of increments for a full rotation of the dose setting member, e.g. 24 increments, or a fraction thereof, e.g. 8 increments. As the dose setting member in most pens is designed to rotate more than a full rotation, e.g. corresponding to 80 increments, the electronics would in both cases have to add increments after having reached the maximum resolution of e.g. 8 or 24 increments. As the display control thus is based on position determination instead of counting as described above, the system is more robust to skipping an input, e.g. during wake-up or if the user rotates the dose setting member very fast.

In addition to the position sensing feature the Gray code arrangement also provides a motion sensing feature, i.e. as long as the detected values changes within a given amount of time a dose can be assumed to be set.

In addition to the position and motion sensing features the Gray code arrangement also provides a wake-up switch arrangement having a low-power sleep mode yet provides a wake-up signal when the code member is rotated during initial dose setting. As the code member inevitably will move during mounting of the add-on module, the Gray code arrangement may also provide a mounting switch which will wake-up the electronics during mounting.

In the shown embodiment the state switch assembly comprises one or more contact members 386 in sliding engagement with the distal portion of the add-on dial member 380 on which a circumferential code ring is arranged, this providing a switch arranged to detect axial movement of the add-on release button 390 between a proximal dose setting state and a distal dose release state. The contact members of both the position sensor and the state switch may be in the form of flexible contact arms which may be provided in the form a combined contact arm array.

In an alternative embodiment (not shown) the axial state switch may be integrated in the position sensor by utilizing the Gray code surface and the contact assembly. More specifically, the cylindrical code member may be arranged to move axially between a proximal position corresponding to a dose setting state and a distal position corresponding to a dose release state, the code member being moved axially by means of the add-on release button. A similar sensor arrangement is disclosed in WO 2010/052275 which is hereby incorporated by reference.

In addition to the state sensing feature the state switch arrangement may also provide a wake-up switch arrangement having a low-power sleep mode yet provides a wake-up signal when the add-on release button is actuated. This arrangement may be relevant during certain operational conditions as will be described below.

Before turning to the description of different use scenarios a further feature of the system will be described. More specifically, the add-module is provided with a memory in which the last rotational position of the scale drum determined by use of the camera is stored. When the add-on module is mounted on a new pen device the memory has to be reset, however, to avoid that the user will have to perform certain operations as part of the initial mounting procedure (as was the case for the FIG. 4 embodiment described above), the add-on module may be provided with an automatic scale drum position capture. More specifically, when it is detected by the mounting switch means that the add-on module has been mounted anew (or for the first time) on a pen device, the camera will capture an image of the scale drum which will be processed to determine the position of the scale drum, e.g. by template matching, and stored in the "last-position" memory. The position can then also be used to display the corresponding current scale drum dose size value on the module display.

During normal use the user will start dialing a dose which will wake up the system which will start adding the actual rotational position to the last-position value stored in memory and display the corresponding value on the module display. The stored value will typically, but not necessarily, be zero. Depending on how fast the system will wake up, how fast the positions during dose setting can be determined, and how fast the user is dialing, the first value shown on the display may not be "1" (in case the position at start is zero), but e.g. 3. As an "absolute" position is determined during dose setting, the system will also be able to handle situations in which a set dose is adjusted, i.e. decreased.

When the system detects that motion has stopped the camera will be operated to capture an image which will be processed to determine the "real" position of the scale drum and display the corresponding value just as the memory will be updated with a new last-position value. Although the system of the second embodiment does not suffer from the above-described issue of skipped increments during dose setting, the calculated and the displayed value may due to slack in the system not correspond to each other, this potentially resulting in the displayed value being adjusted based on the camera capture. However, due to system design this should not be more than one increment. The user may desire to further adjust the dose which will result in a new image being captured when motion is detected to have stopped.

At this point the system is awake and waiting for the set dose to be released, however, after e.g. 5 minutes without activity the system may return to sleep mode. To wake up the system when the set dose is released by actuating the add-on release button, input from the state switch may be utilized. As the dose setting member and thus the position sensor is not moving during out-dosing there will be no motion activity input to wake up the system. Alternatively the system may first wake up when the add-on release button returns to the proximal dose setting position.

When the user after or during dose expelling releases the add-on release button the state switch will detect the change and control the camera device to capture an image of the scale drum. If the scale drum position is determined to be at the end-of-dose zero position it can be assumed that the set dose has been fully expelled and that the size of the expelled dose correspond to the last-position value stored in memory. The display may then display the value together with information indicating that the shown value corresponds to an expelled dose, e.g. by displaying an associated time stamp. The data will be stored as a log entry in the module memory. If the camera-captured scale drum position does not correspond to the end-of-dose position the system will at first assume that expelling of the set dose has been paused and await further activity. In order to not confuse the user to assume that the set dose has been fully expelled, the display may not show the value corresponding to the current scale drum position but instead a pause symbol. If no activity is detected the system will after a given amount of time, e.g. 5 minutes, time out and calculate an expelled dose size as the difference between the set dose amount (corresponding to the last-position value) and the remaining dose amount (corresponding to the present-position value). The calculated dose size will be displayed and stored as a log entry. The previous last-position value will be over-written with the present-position value.

If the user at this point decides to expel the remaining dose, the system will wake up and determine a further expelled dose amount, e.g. corresponding fully or partly to the remaining dose amount. Alternatively, the user may decide to cancel the remaining dose fully or partly by dialing the add-on dial member towards the initial zero position. As the position sensor system is activated the display will be activated and the dose size corresponding to the current position will dynamically be shown in the display. When it is detected that rotational motion has stopped the camera will be operated to capture an image. As the state switch has not been operated the new captured position value, e.g. zero, will be stored in memory as a new last-position.

In addition to provide input during operation of the pen device, the state switch may also be used to control the add-on module to display stored log entries.

As appears, by the sensor set-up of the second embodiment an add-on logging device is provided which is both user-friendly and power-efficient in use.

Figure 6:
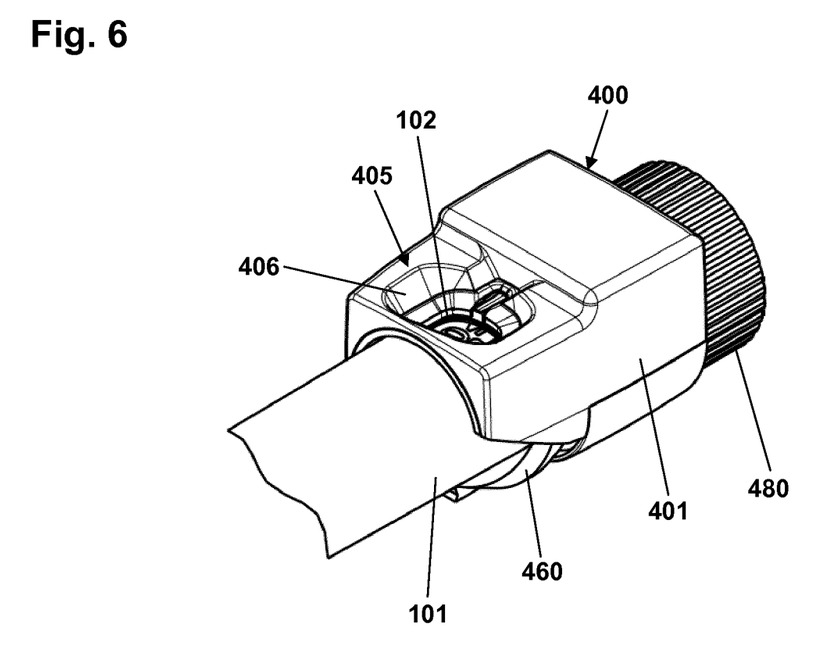
FIG. 6 shows a further add-on device mounted on the housing of a drug delivery device.

FIG. 6 shows schematically an add-on device 400 in a state where it has been mounted on the housing 101 of a drug delivery device of the above-described pen type. As appears, the add-on device 400 is provided with an open cavity allowing a user to observe the scale drum during operation of the drug delivery device. Correspondingly, the add-on device does not comprise a display.

The add-on device 400 as shown comprises a housing 401 with a cavity 405 having a lower camera opening adapted to be positioned over and in alignment with the housing display window 102. A camera (not shown) is arranged to capture an image of at least a portion of the scale drum. The opening is surrounded by a positioning structure in the form of a downwardly protruding lip portion 406 adapted to precisely engage and grip the chamfered edge portion 109 of the display opening, this ensuring that the add-on device can be correctly positioned on the pen housing. As explained in greater detail in EP 15202796.7 the lip portion in the shown embodiment does not fully cover the edge portion surrounding the window opening. Apart from the missing display the add-on device of FIG. 6 is similar in design to the above-described add-on device described with reference to FIG. 5. Correspondingly, the add-on device 400 is provided with a combined add-on dial and release member 480 as well as a rotary sensor assembly and a state switch. The add-on device further comprises a user-operatable locking member 460. The locking member may be designed to prevent locking until the add-on device is correctly positioned on the pen housing with the lip portion seated in the housing display opening. The mounting switch may be arranged to be actuated when the locking member is actuated to its fully closed position.

In the embodiment of FIG. 5 the rotary sensor assembly was used to provide input for controlling the display, however, the output from the rotary sensor assembly may also be used for other purposes. More specifically, in the add-on device 400 scale drum position is determined by template-matching with a stored representation of the entire scale drum surface image.

Figure 7:
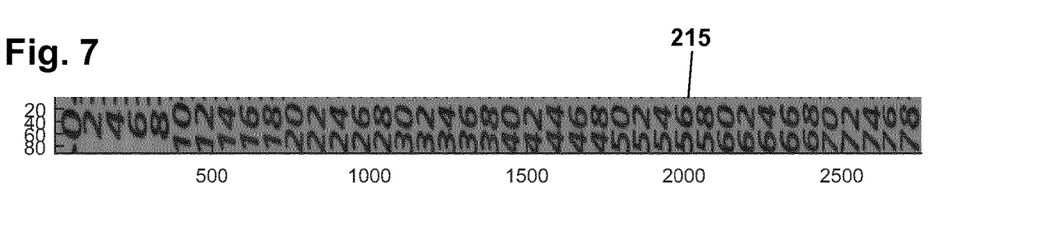
FIG. 7 shows a scale drum reference representation.
Figure 8:
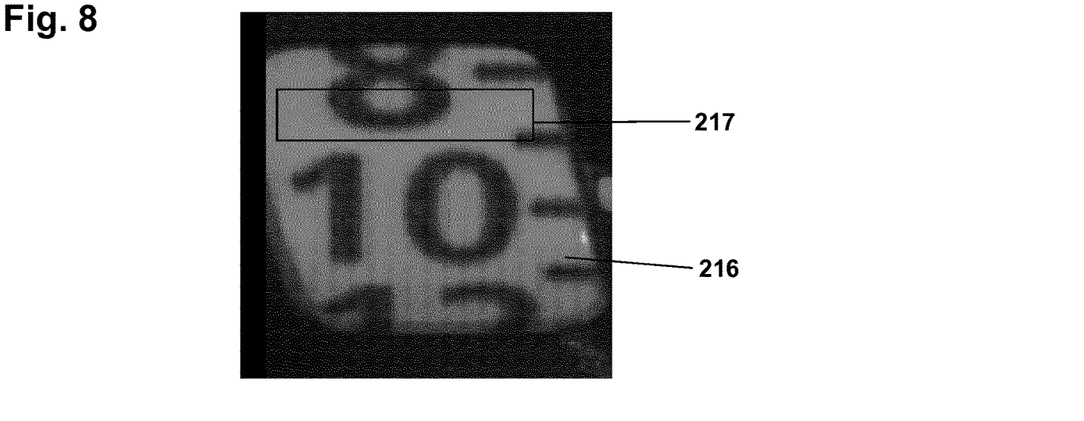
FIG. 8 shows an image capture from a scale drum.
Figure 9:
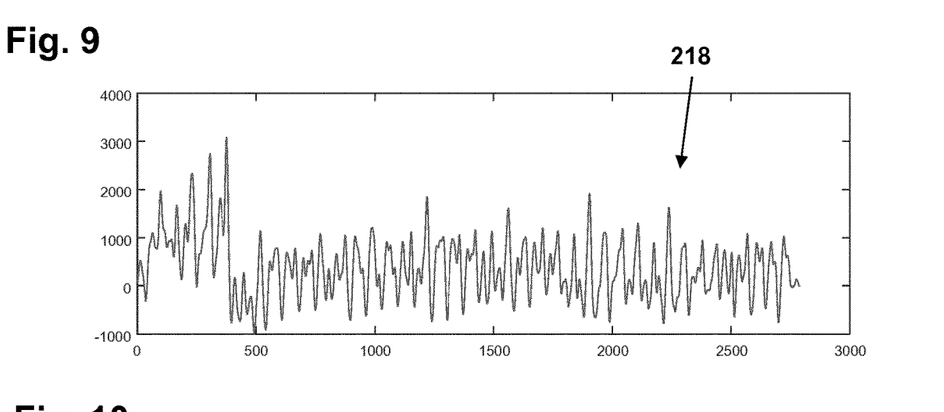
FIG. 9 shows cross correlation of the FIG. 8 image portion to the reference representation.
Figure 10:
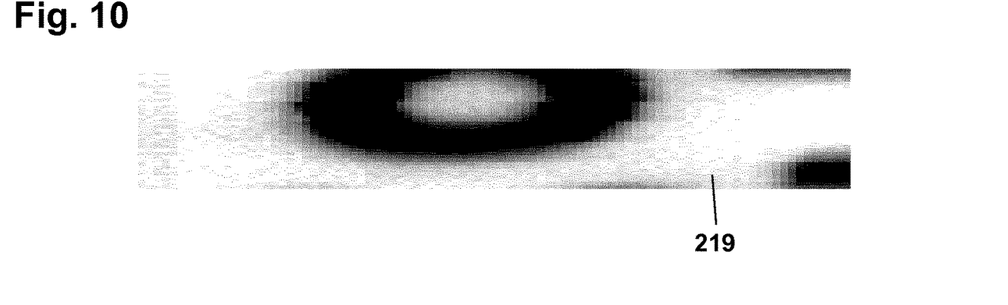
FIG. 10 shows a matched portion of the reference representation.

Correspondingly, FIG. 7 illustrates a template image 215 of the whole scale-drum, obtained by concatenating parts of successive images from a film where the scale-drum moves from position 80 to position 0. The template image is used as a reference when to determine the position of a specific image. The pixel position (horizontal axis in the above figure) corresponds to the drum position (in degrees, IU or other units). As an example, FIG. 8 shows an image 216 of the scale-drum window where the position corresponds to 10 IU, the rectangle 217 illustrating the area that is used for position detection. FIG. 9 then shows the cross correlation of the rectangle image portion to the reference 115 as a function 118 of pixel position. Searching for the peak reveals a best match at pixel position 341, corresponding to the cut 119 from the reference image as shown in FIG. 10. The reference image at this pixel offset was taken when the scale drum was in a position 9.8 IU.

To speed up the search procedure to save time and enhance power efficiency the search may advantageously begin at the position representing the most likely value and, at least initially, only consider a given limited range around that position. Thus the electronic circuitry of the FIG. 6 embodiment is provided with a memory adapted to store a reference position value corresponding to the most recent known rotational position of the indicator, and the processor means is adapted to (i) determine a current rotational position of the indicator based on: a captured image of the indicator, the stored reference position value, and the amount of rotational movement detected by the sensor assembly since the position value was stored, (ii) store the determined current rotational position in the memory as a new reference position value, and (iii) determine an expelled dose amount based on inputs from the camera as described above. Also in case rotational position of the indicator is based on OCR it may help improve efficiency and accuracy of the OCR process if information of the most likely rotational position is known.

Indeed, the above-describe concept for more efficient determination of the rotational position of the indicator may also be utilized with the same effect in an add-on device comprising a display as described with reference to FIG. 5.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An add-on device adapted to be releasably attached to a drug delivery device, the drug delivery device comprising:
   a housing,
   a drug reservoir or structure for receiving a drug reservoir,
   a drug expelling structure comprising a moveable dose setting member allowing a user to set a dose amount of drug to be expelled,
   an actuation member actuatable between a first and a second state, the first state allowing a dose amount to be set, the second state allowing the drug expelling structure to expel a set dose, and
   an indicator adapted to display the set dose amount during dose setting, and to display the remaining dose amount to be expelled during drug expelling,
the add-on device comprising:
   a mounting structure,
   an electronically controlled display adapted to display a set dose amount, a sensor assembly adapted to detect movement of the dose setting member when the add-on device is attached to a drug delivery device, a camera device adapted to capture an image of the indicator, a processor structure adapted to:
(i) control the display dynamically to show the set dose amount based on input from the sensor assembly, and
(ii) determine an expelled dose amount based on input from the camera device, a dial portion adapted to be releasably attached, directly or indirectly, to the moveable dose setting member, a release portion adapted to be moved by the user between an initial and an actuated position, and wherein the release portion is adapted to move axially relative to the dial portion.

2. An add-on device as in claim 1, wherein an expelled dose amount is determined based on a first feature captured from a first image and a second feature captured from a second image, the first image being captured when a dose amount has been set and the second image being captured when a dose amount has been expelled.

3. An add-on device as in claim 2, wherein the first feature is used to determine a first position of the indicator, and the second feature is used to determine a second position of the indicator, a positional difference between the first and second positions being indicative of an expelled amount of drug.

4. An add-on device as in claim 1, wherein the processor is adapted to:
control the camera device to capture a first image when no input has been received from the sensor assembly for a predetermined amount of time after the last input.

5. An add-on device as in claim 1, further comprising a switch structure adapted to detect when the actuation member is actuated from the second to the first state,
wherein the processor is adapted to control the camera device to capture a second image when the switch structure detects that the actuation member is actuated from the second to the first state.

6. An add-on device as in claim 1, further comprising a memory adapted to store a reference position value corresponding to a rotational position of the indicator, the processor structure being adapted to:
(i) determine a current rotational position of the indicator based on: a captured image of the indicator, the stored reference position value, and the amount of rotational movement detected by the sensor assembly since the position value was stored,
(ii) store the determined current rotational position in the memory as a new reference position value, and
(iii) determine an expelled dose amount based on input from the camera device.

7. An add-on device as in claim 1, comprising:
a main portion adapted to be releasably attached to the housing, and
the sensor assembly comprising:
a first portion coupled to the main portion, and
a second portion coupled to the dial portion,
wherein the sensor assembly is adapted to detect rotational movement between the first and second portion.

8. An add-on device as in claim 7, wherein:
the add-on device is adapted to cover the dose setting member when attached to a drug delivery device, and
the dial portion is adapted to be gripped by the user to thereby move the dose setting member.

9. An add-on device as in claim 8, wherein:
the dial portion is adapted to rotate to thereby rotate the dose setting member, and
the sensor assembly is a rotary sensor assembly.

10. An add-on device as in claim 7, wherein the dial portion has an initial axial position, the dial portion being restricted from being moved proximally relative to the main portion.

11. An add-on device as in claim 7, further comprising:
wherein the release portion with the add-on device attached to a drug delivery device is adapted to engage and move the actuation member.

12. An add-on device as in claim 11, wherein:
the add-on device is adapted to cover the actuation member when attached to a drug delivery device.

13. An add-on device as in claim 11, wherein the dial portion is adapted to rotate to thereby rotate the dose setting member.

14. An add-on device as in claim 11, wherein the dial portion is coupled to and moves axially together with the release portion.

15. An add-on device as in claim 1 in combination with a drug delivery device as in claim 1.

* * * * *

UNITED STATES PATENT AND TRADEMARK OFFICE
CERTIFICATE OF CORRECTION

| | |
|---|---|
| PATENT NO. | : 10,946,144 B2 |
| APPLICATION NO. | : 16/081365 |
| DATED | : March 16, 2021 |
| INVENTOR(S) | : Nielsen |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Thirty-first Day of January, 2023

Katherine Kelly Vidal
*Director of the United States Patent and Trademark Office*